(12) United States Patent
Plaschke (10) Patent No.: US 6,409,996 B1
(45) Date of Patent: Jun. 25, 2002

(54) COMPOSITION COMPRISING ONE OR MORE FLAVONOIDS, METHOD OF OBTAINING SUCH COMPOSITION AND USE THEREOF AS UV-ABSORBING AGENT

(75) Inventor: Kim Plaschke, Næstved (DK)

(73) Assignee: Flavone Sunproducts A/S, Naestved (DK)

( * ) Notice: Subject to any disclaimer, the term of this patent is extended or adjusted under 35 U.S.C. 154(b) by 0 days.

(21) Appl. No.: 09/554,763

(22) PCT Filed: Nov. 19, 1998

(86) PCT No.: PCT/DK98/00505

§ 371 (c)(1),
(2), (4) Date: May 19, 2000

(87) PCT Pub. No.: WO99/25316

PCT Pub. Date: May 27, 1999

(30) Foreign Application Priority Data

Nov. 19, 1997 (DK) .............................................. 1316/97

(51) Int. Cl.[7] .............................. A61K 7/42; A61K 7/00; A61K 31/35
(52) U.S. Cl. ......................... 424/59; 424/401; 514/456; 514/944
(58) Field of Search ................... 424/401, 59; 514/456, 514/944

(56) References Cited

U.S. PATENT DOCUMENTS

| | | | | |
|---|---|---|---|---|
| 4,297,348 A | * | 10/1981 | Frazier ........................ | 424/180 |
| 4,497,838 A | * | 2/1985 | Bonnell ....................... | 426/429 |
| 4,617,293 A | * | 10/1986 | Wahlig et al. ................ | 514/41 |
| 4,786,498 A | * | 11/1988 | Isaac et al. ................... | 424/195.1 |
| 5,192,277 A | * | 3/1993 | Chung et al. ................ | 604/360 |
| 5,650,433 A | * | 7/1997 | Watanabe et al. ........... | 514/456 |
| 5,660,818 A | * | 8/1997 | Dubief et al. ................ | 424/70.1 |
| 5,660,832 A | * | 8/1997 | Steiner et al. ............... | 424/195.1 |
| 5,665,367 A | | 9/1997 | Burger et al. | |
| 5,780,060 A | * | 7/1998 | Levy et al. .................. | 424/489 |
| 5,789,581 A | * | 8/1998 | Matsuura et al. ........... | 536/128 |
| 5,858,371 A | * | 1/1999 | Singh et al. ................. | 424/195.1 |
| 6,121,243 A | * | 9/2000 | Lanzendorfer et al. ....... | 514/28 |
| 6,147,054 A | * | 11/2000 | De Paoli Ambrosi ......... | 514/23 |

FOREIGN PATENT DOCUMENTS

| | | | |
|---|---|---|---|
| EP | 0774249 | | 5/1997 |
| JP | 57035506 A | * | 2/1982 |
| JP | 403005423 A | * | 1/1991 |
| JP | 06113871 A | * | 4/1994 |
| JP | 07138171 A | * | 5/1995 |
| JP | 40828830 A | * | 10/1996 |
| NZ | 264108 A | * | 5/2001 |
| WO | 9618379 | | 6/1996 |
| WO | 9618382 | | 6/1996 |

OTHER PUBLICATIONS

Abstract of JP–55111411A of Sansei Seiyaku KK for "Cosmetic Powder White Skin Prevent . . . Component," 2/79.
Abstract of JP 63–96120B of K. Iwashima for "Anti–Suntan Cosmetic," 4/88.
Chemical Abstracts vol. 127, No. 17, 238967m, to S. Yoon et al., for "Selective Adsoprtion of Flavonoid Compounds from the Leaf Extract of Ginkgo Biloba Leaves," 1997.
Chemical Abstracts vol. 126, No. 16, 211294g, to M. Calvarano et al., for "Naringin Extraction from Exhausted Bergamot Peels," 1996.
Chemical Abstracts vol. 126, No. 9, 119332v, to Z. Liu et al., for "A Method for Water Extraction of Total Flavone from Ginkgo Biloba Leaves," 1996.

* cited by examiner

*Primary Examiner*—Jose' G. Dees
*Assistant Examiner*—Marina Lamm
(74) *Attorney, Agent, or Firm*—Dykema Gossett PLLC (57) ABSTRACT

A flavonoid-containing sunscreen composition having UV absorbency at 282 nm in water contains at least one flavanone and at least one flavone, the flavanone providing 75 to 98% of the UV absorbency at 282 nm and the flavone providing 2 to 25% of the absorbency at 282 nm. The composition is formed of flavonoids extracted from citrus fruit using water, and separating the extracted flavonoids using a sorbent material, and then recovering the flavonoids from the sorbent material using a solvent.

27 Claims, 4 Drawing Sheets

COMPOSITION COMPRISING ONE OR MORE FLAVONOIDS, METHOD OF OBTAINING SUCH COMPOSITION AND USE THEREOF AS UV-ABSORBING AGENT

BACKGROUND OF THE INVENTION

1. Field of the Invention

The present invention relates to a composition that contains one or more flavonoids, a method of obtaining such composition, and the use thereof as UV-absorbing agent, i.e., for producing a sunscreen product.

2. The Prior Art

In the art of sunscreen production it has been found that flavonoids may be used in order to enhance absorption of UV-radiation.

The abstract of Japanese document JP-55-111411-A discloses the use of flavonol in cosmetics for the purpose of protecting against sunburn.

Another effort to use a flavonoid as a sun protecting agent is disclosed in Japanese patent abstract JP-63-96120A, which describes an anti-suntan cosmetic including i.a. a flavone derivative and/or a coumarine. Unfortunately, coumarines are known to be skin irritating and are generally an unwanted substance in products for dermatological use.

It is furthermore known from the article "Orange Peel Wax", Cosmetics & Toiletries magazine vol. 109, august 1994, that the wax extracted from oranges comprises flavonoids, carotenoids and unsaturated monoesters, and that these compounds have strong UV-absorptive properties.

The sun emits UV-radiation having wavelengths in the area of 200 nm to 400 nm. This area is commonly subdivided into 3 different bands designated UV-A (320 nm–400 nm), UV-B (290 nm–320 nm) and UV-C (200 nm–290 nm) respectively. Most of the UV-radiance reaching the earth is UV-A (about 90%). UV-B is only represented by about 10% of the UV-radiance but, due to its high energy level, it causes about 98% of the erythema of humans, while UV-C, having the highest energy level, is nearly totally blocked by the ozone in the atmosphere.

Modern research into the causes of skin cancer indicates that this UV-radiance, and particularly UV-B, may cause long term damage to skin cells, e.g., in terms of damage to cell DNA, eventually resulting in skin cancer.

Thus, many prior art sunscreen products aim to protect primarily against UV-B. Wearing a sunscreen product, people tend to expose A) themselves to direct sunlight for extended periods of time, counting on the protection offered by the sunscreen. However, long term influence by UV-A may cause accelerated aging of the skin and is also recognized as eventually causing skin cancer.

This problem is partly addressed in PCT application WO 96/18382 which discloses a cosmetic and/or dermatological composition for preventing harmful effects on human skin due to UV-radiation. The composition comprises one or more flavonoids or their glucosides and preferably also both a cinnamon acid derivative and an anti oxidizing agent such as vitamin E. The flavonoids can, according to WO 96/18382, be obtained as various plant extracts, and are preferably flavonones, e.g., naringin and hesperidin.

PCT application WO 96/18379 discloses a cosmetic and/or dermatological composition for preventing oxidative damaging of hair and skin such as stinging or sensible skin. The composition is essentially the same as disclosed in WO 96/18382 and comprises one or more flavonoid components optionally combined with a cinnamon acid derivative and an anti oxidizing agent.

The documents WO 96/18382 and WO 96/18379 furthermore suggest the use of additional UV-B absorbing components in order to obtain a higher absorption in the UV-B-range.

However, the suggested compositions comprising mainly flavanones such as naringin and hesperidin combined with cinnamon acid derivatives and/or further UV-B absorbers has proven to more or less entirely block the UV-radiation in the UV-B range, but not to provide an adequate protection of the skin in i.a. the UV-A range, and the provided absorption profiles seem merely arbitrarily selected.

As many people sunbathe in order to tan their skin and UV-radiance plays an important role in the tanning process, it is thus desirable to provide a sunscreen product enabling both tanning and at the same time offering substantial protection of the skin cells. However, as indicated above, the prior art documents do not provide a UV-absorbing composition having such a satisfactory profile for both protecting human skin cells and at the same time allowing the skin to tan.

There thus remains a need for a composition having a optimized UV-absorption profile, so as to block and/or absorb essentially the most damaging wavelengths in a carefully balanced way while still allowing the skin to tan and furthermore without subjecting the skin to unwanted substances.

Therefore it is an object of the present invention to overcome the shortcomings of in particular the above mentioned prior art and to provide such an optimized UV-absorbing composition.

SUMMARY OF THE INVENTION

This object is obtained by the composition according to the invention characterized in that it includes at least one flavonone and at least one flavone and having an UV-absorbency at 282 nm in water where the flavanone(s) accounts for 75–98% of the flavonoids absorbency, and where the flavone(s) accounts for 2–25% of the flavonoids UV-absorbency at 282 nm in the composition.

This first aspect of the invention is based on the recognition that flavanones are particularly effective as UV-B-filters and flavones are particularly effective as UV-A-filters, and the recognition that a particularly advantageous composition of flavanones and flavones exists, where said composition of flavonoids has an absorbency profile in terms of UV-radiation at specific wavelengths, which profile matches the degradation profile of human skin cell DNA, in terms of the composition having the most intense absorbency at the wavelengths where the DNA is most vulnerable.

It has thus for the first time been realized that by matching the profile of human skin cell DNA degradation as a function of UV-wavelengths with a substantially inverse absorption profile, it is possible to exactly filter out the most damaging wavelengths and at the same time allow the skin to tan.

It has furthermore surprisingly been found that this criterion is met by a composition comprising at least one flavanone and at least one flavone, in which composition the flavanone part preferably represents about 75–98% of the flavonoids UV-absorbency in water at 282 nm, and the flavone part preferably represents about 2–25% of the flavonoids UV-absorbency in water at 282 nm.

The term "flavonoids UV-absorbency" designates the total amount of UV-absorbency caused by the flavonoids in the composition.

Preferably the flavanones account for 78–90% of the absorbency and the flavones account for 2–10% of the flavonoids absorbency in water at 282 nm, and more preferably the flavanones account for 80–85% of the absorbency and the flavones account for 3–5% of the flavonoids absorbency in water at 282 nm.

The further 10–17% absorbency may be provided by the same and/or other substances, e.g., carotenoids; however, this further absorbency is preferably provided substantially by other flavonoids, and even more preferably substantially by flavanones, flavanoles and/or flavones.

According to a preferred embodiment of the composition according to the invention the composition comprises at least one flavanone and at least one flavone, where said flavanone(s) accounts for 75–98% of the flavonoids absorbency, and where said flavone(s) accounts for 2–25% of the flavonoids UV-absorbency at 282 nm in an aqueous solution of the composition.

This particularly advantageous ratio between flavanone and flavone is obtained when the respective absorbency at 282 nm for flavanone and flavone is as disclosed above.

It is furthermore, preferable if the ratio between flavanones and flavones in dry weight (solids content) is around between 50:1 to 2:1, more preferable around 30:1 to 5:1 and even more preferable around 25:1 to 10:1, and in particular around 20:1.

Figure 1:
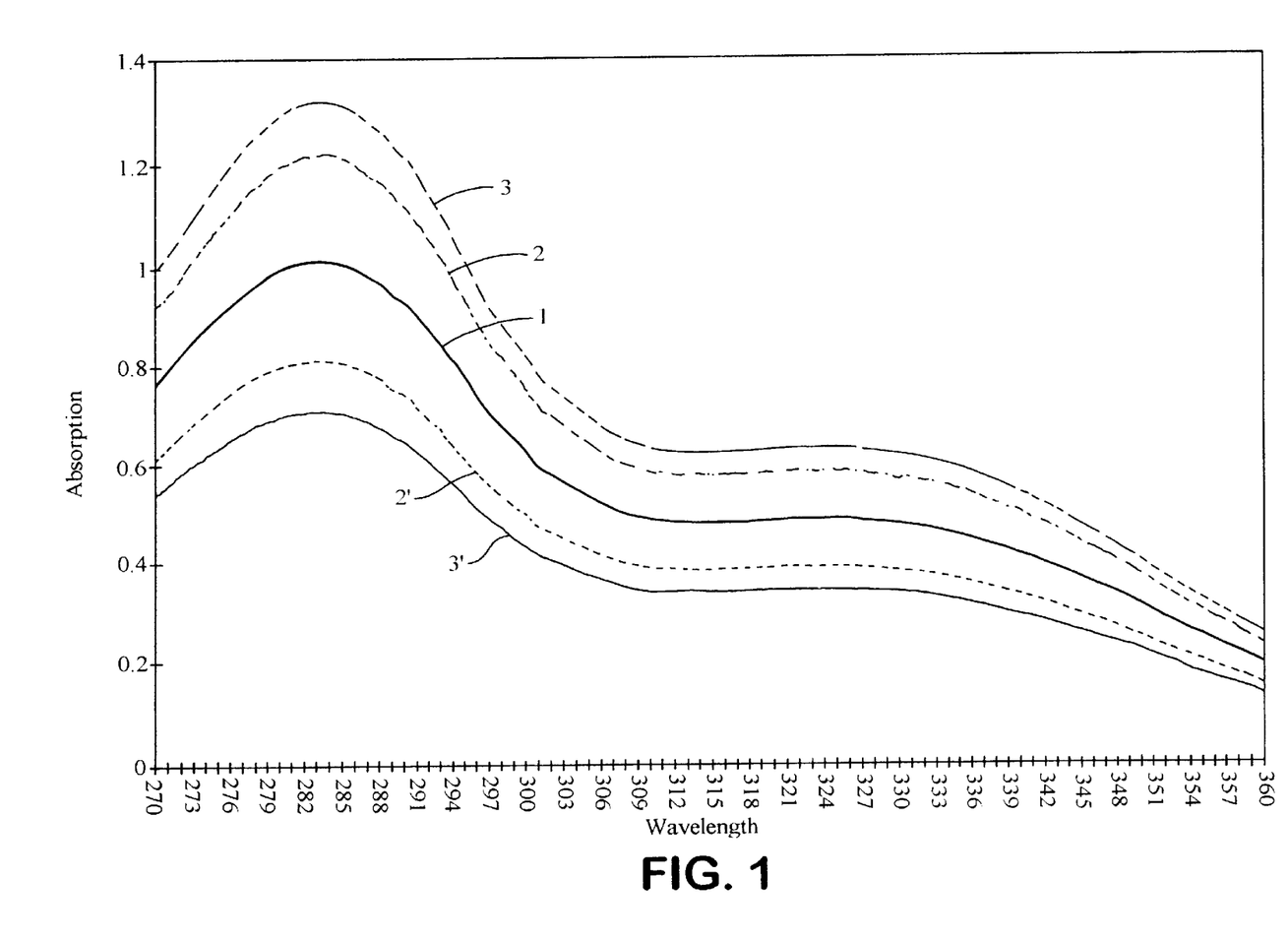
FIG. 1 depicts the preferred UV-absorption profile.

It has even further been recognized that the above disclosed objective may be accomplished by a composition of flavanoids and particularly defined as comprising at least one flavanone and at least one flavone, which composition is characterized in that the flavonoids have a UV-absorption profile in water in the wavelength range 270–360 nm and at a total flavonoid concentration of 20–30 μg/ml, preferably about 25 μg/ml, said profile substantially falling within the +/−30% limits of the profile in FIG. 1. Preferably the said profile substantially falls within the +/−20% limits of the profile in FIG. 1.

Said composition of flavonoids preferably comprise at least one flavanone-based and at least one flavone-based compound selected from naringin (naringenin-7β-neohesperidoside; 5,7,4'-trihydroxyflavanone-7β-neohesperidoside) and/or neohesperidin (hesperitin-7β-neohesperidoside; 5,7,3'-trihydroxy-4'-methoxyflavanone-7β-neohesperidoside) and/or neoeriocitrin (eriodictyol-7β-neohesperidoside; 5,7,3',4'-tetrahydroxyflavanone-7β-neohesperidoside) and/or isonaringin (isonaringenin-7β-neohesperidoside; 5,7,4'-trihydroxyisoflavanone-7β-neohesperidoside) and rhoifolin (apigenin-7β-neohesperidoside; 4',5,7-trihydroxyflavone-7β-neohesperidoside) and/or luteolin-7β-neohesperidoside (5,7,3',4'-tetrahydroxyflavone-7β-neohesperidoside and/or veronicastroside) and/or neodiosmin (5,7,3'-trihydroxy-4'-methoxyflavone-7β-neohesperidoside). Other known flavanones and flavones, e.g. those mentioned in "The flavanoids, Advances in research since 1986", J. B. Harborne, Chapman & Hall 1$^{st}$ ed. 1994 can be utilized according to the invention, but the above mentioned have proven to be particularly advantageous.

It has been found that the particularly advantageous UV-absorption profile may be obtained by a composition comprising the flavonoids naringin, neohesperidin, neoeriocitrin, isonaringin and rhoifolin. Particularly compositions comprising a flavanone having substantially the absorption profile of naringin or neohesperidin and a flavone having substantially the absorption profile of rhoifolin are preferred. Naringin or neohesperidin being the most preferred flavanone(s) and rhoifolin being the most preferred flavone. Rhoifolin has proven to be particularly advantageous to apply in order to obtain a suitable absorption profile also in the UV-A-range.

It is generally preferable that the mentioned compounds are present in a substantial amount, i.e. an amount capable of substantially affecting the UV-absorbency profile of the composition.

According to a preferred embodiment of the composition according to the invention, each of the above mentioned flavonoids account for an amount of the UV-absorption of the composition at 282 nm in water corresponding to naringin and/or neohesperidin: 60–80%, neoeriocitrin: 5–15%, isonaringin 1–10% and rhoifolin 1–10%.

According to a preferred embodiment of the composition according to the invention the ratio between the absorbency at 282 nm and the average absorbency at 320–324 nm is about 1.8–2.4 in water.

The noted ratio has proven particularly advantageous in terms of protection skin cell DNA from deteriorating.

A preliminary clinical test conducted on 8 persons at a dermatological clinic indicated the following: A concentration of the flavonoid product in a UV-neutral cream of 0.75%–1% equaled a sun protection factor of 4 (DIN standard). A concentration of the flavonoid product in a UV-neutral cream 1.5% equaled a sun protection factor of 8 (DIN standard).

When determining the absorbency of a composition comprising flavonoids according to the invention, it is preferred that the concentration of the composition is adjusted in such a way that the most intense absorbency in the absorbency spectrum is less than and/or about 1. Even more preferable the absorbencyis measured within a concentration range where the absorbency is linear dependent on the concentration of the flavonoids in the composition. This is typically the case in the absorbency range up till about 1. The sample may be concentrated or diluted if necessary to obtain linearity such.

Flavonoids are generally very suitable as sunscreen agents because they, apart from their UV-absorbency, are both non-toxic and extremely stable. Many prior art chemical compounds used as sunscreen agents decompose over time and/or due to the high energy of the UV-radiation, and the decomposition products are in many cases skin-irritating, toxic or even carcinogenic.

The present invention also relates to dermatological applicable products, e.g. a sunscreen product, comprising a composition of flavonoids according to the invention and further excipients. These excipients comprising all generally known components in the art of producing sun tan lotions, moisturizing lotions and cosmetics, e.g. day cremes, particularly such water based compositions. Such lotions, cremes and the like are also comprised by the use of the composition according to the invention.

It is also according to an embodiment of the invention possible to use the composition according to the invention as enhancers for known UV-absorbing agents, thus lowering the required amount of these in order to obtain a certain absorption. However, it is generally preferable to use the composition of flavonoids according to the invention as substantially the only essential UV-absorbing agents in sun screen products, i.e. without cinnamon acid derivatives, coumarines, vitamin E and the like.

It is a further object of the present invention to provide a process for the preparation of a composition of flavonoids having the above mentioned advantageous properties.

It is generally known to extract flavonoids from various plant material and several processes for obtaining the flavonoids has been suggested. However, it seems that no known process provides a composition as suggested above per se.

Furthermore, it seems that if substantially pure flavones and flavanones are mixed in water, their solubility is far less than desirable for suitable application as UV-absorbers in water based sun screen lotions.

It is thus also an object of the invention to overcome these problems and the further problems discussed below with the prior art processes.

The article "Anti-erythematous and photoprotective activities in guinea pigs and in man of topically applied flavonoids from *Helicrysum Italicum G. Don.*", Acta Therapeutica 14 (1988), discloses the use of flavonoids as a means to avoid or treat erythematous skin. Furthermore the article discloses a method of extracting flavonoids from the plant "*Helicrysum Italicum G. Don*" using dried leaves from the plant. The leaves are milled and percolated in a mixture of 70% ethanol in water. The thus obtained ethanol-based extract is concentrated by evaporation, and the concentrate is dissolved in methanol by vigorous stirring and left to stand overnight in the dark and subsequently filtered to remove unwanted substances. The methanol-based extract is fully evaporated and the solids are suspended in destined water and subjected to solid-phase chromatography elution using petroleum ether. Further elution using n-hexane removes lipophilic substances and the fraction comprising the flavonoids is obtained from the column by elution using ethyl-acetate, which is subsequently evaporated using vacuum.

Chemical abstracts vol. 127, no. 17, 238967m, discloses a process for extracting the total amount of flavone from ginko biloba leaves. The process comprises extraction of flavonoids from dried ginko biloba leaves with methanol and purification using the polycarboxyl ester resin XAD-7 from a water/methanol mixture. The abstract also discloses that the pH did not effect the adsorption of the flavonoids, but at high pH the chemical structure of the flavonoids was changed. Also the polarity of the solvent is discussed.

Due to environmental reasons it is generally undesirable to use large quantities of organic solvents such as methanol for extracting the flavonoids at industrial scale levels.

Furthermore, as discussed earlier it is generally desirable to make cosmetics, i.a. sunscreen products, which in essence is aqueous-based or gel-based rather than based on organic solvents and/or oils. This i.a. being due to undesirable side-effects of many such organic solvents. By using organic solvents for extracting the flavonoids as disclosed above, also unwanted and/or toxic substances are extracted. It is thus necessary to apply a costly purification step in order to obtain an applicable flavonoid fraction.

From U.S. Pat. No. 2,421,061 it is furthermore known to obtain flavanones from plant material by preparing a pulp of the material and adding a sufficient amount of calcium hydroxide to the pulp to cause a hardening thereof, dissolving the pulp in water containing a substantial amount of slaked lime and enough caustic soda to adjust pH to about 8.4–11.4, subjecting the pulp to a pressing in order to remove solid material and treating the remaining liquid phase with acid to precipitate the flavanones as crystals, which are removed as the product.

U.S. Pat. No. 2,442,110 discloses a similar process for obtaining hesperidin crystals from orange pulp.

However, it appears that a flavonoids obtained by the highly basic extraction of flavonoids suggested in U.S. Pat. Nos. 2,421,061 and 2,442,110 have a very low solubility.

Chemical abstracts vol. 126, no. 16, 211294g, discloses a process for extracting naringin from exhausted bergamot peels. The process comprises extracting the naringin from the peels by means of hot water and purifying the naringin through ultrafiltration and resin adsorption. However, ultrafiltration also seems to impair the flavonoids solubility significantly.

Chemical abstracts vol. 126, no. 9, 119332v, discloses a process for extracting the total amount of flavone from ginko biloba leaves. The process comprises repeated extraction with water and purification through chromatography using a polyamide resin as adsorbent and ethanol as eluent. This process only extracts the flavone content of the ginko biloba and is both slow and troublesome.

Unfortunately, neither the flavonoid-containing orange peel wax discussed in the introduction nor the flavonoid-containing fractions obtained by the above mentioned methods exhibit sufficient solubility in water for practical application of the flavonoids as an active substance in a substantially water-based cosmetic product, i.e. as a sunscreen agent.

Furthermore, apart from the above mentioned deficiencies of the prior art methods they are generally all both slow and troublesome, and thus not suitable for industrial scale production.

Accordingly it is an object of the present invention to overcome the stated problems and to obtain a method of preparing a composition of flavonoids suitable for use as an active ingredient in a sunscreen product and being sufficiently soluble in water to enable the production of an essentially water- and/or gel-based sunscreen product.

These objects are obtained by the method according to the invention, wherein a flavonoid containing raw material is treated with an extraction medium to obtain an extract and wherein said composition is separated from said extract by absorption and/or adsorption, characterized in comprising the steps of
 a) extracting the flavonoids by means of an aqueous medium at a temperature between 20 and 60° C. and at a pH at or below 7,
 b) separating the flavonoids from the extract by adsorption or absorption by means of a sorbent-material at a pH below 7, and
 c) obtaining the flavonoids from the sorbent-material by means of a solvent.

It has surprisingly been found that the flavonoids may be extracted directly from the flavonoid-containing raw material using water or a substantially aqueous medium as the extraction medium and that the flavonoid-comprising fraction may be separated from the thus obtained aqueous extract in an advantageously both gentle and efficient manner using adsorption and/or absorption within the prescribed temperature range and at the prescribed pH.

The extraction may be performed in any way that enables the flavonoids of the raw material to migrate to the extraction medium, e.g. it may be performed as a percolation step, by suspending the raw-material in the extraction medium and/or by solvating the raw-material in the aqueous extraction medium. Preferably the extraction medium is stirred during the extraction step.

In this way it is possible to avoid the use of organic solvents and thus reduce the environmental risk as well as the cost of the process.

It is a further advantage of the method according to the invention, that when using water for the extraction step according to the invention, it seems that the amount of several unwanted substances is decreased significantly compared to the prior art methods. Such substances comprises e.g., coumarines, which are known to be photo-toxic, and skin-irritating terpenes. In this way further purification of the product is unnecessary and both time and money is saved. It is furthermore not necessary to apply a process step to remove lipophilic substances.

The pH of the extraction medium is preferably unadjusted, thus resulting in a pH value of about 7 for substantially pure water. However, the extraction medium may comprise salts and/or other solutes that may affect the pH value. It is in these cases preferable to adjust the pH-value to 7 or below.

The pH of the extract is accordingly also preferably unadjusted. Depending of the raw-material the pH is typically and preferably around 1 to 6 and more preferably around 2 to 5. Within this range it is possible to obtain the desired composition comprising flavonoids using the method according to the invention.

The pH of the extraction medium and/or the extract may as mentioned be adjusted, and at some pH-values some of the flavonoids may crystallize. According to the invention it is preferred to keep the flavonoids solubilized in the extract at any time up till the absorption/adsorption and the pH-value of the extract should be adjusted accordingly. Within the above mentioned pH-range no precipitation of flavonoids are observed by the method according to the invention.

The extraction and the separation may be carried out at any temperature within a wide temperature range, i.e. as long as the extraction medium and the extract is liquid. Preferably these steps are carried out at temperatures between 5–75° C. However it has surprisingly been found that there is an optimum temperature in terms of yield for the extraction step ranging from 40 to 70° C., preferably from 45 to 60° C., more preferably at temperatures around 50–55° C. This is particularly true when extracting on immature citrus fruits. However, when extracting on mature or very mature citrus fruits the preferred temperature is generally lower e.g. between 5–55° C., preferably 10–40° C. and more preferably 20–30° C.

Generally it has thus proven desirable to operate at a temperature of between 20 and 60° C.

The flavonoid fraction may be separated from the extraction medium by any known adsorption and/or absorption method, e.g., by bringing the extract in contact with a sorbent-material.

According to a preferred embodiment of the method according to the invention the extract comprising the flavonoid(s) is subjected to a solid-phase adsorption and/or absorption using a sorbent comprising separation reactor, in which the flavonoid fraction is adsorbed to and/or absorbed by the sorbent-material. During the separation step, it is preferred to stir the content of the separation reactor.

In order to prevent the pipes and valves from being stopped by solid material, it is preferred to filter the extract before subjecting it to the separation.

As sorbent-material may be used any sorbent-material capable of retaining the desired flavonoid-containing fraction. Preferably the sorbent-material is a non-ionic polymeric adsorbent, e.g. a cross-linked moderately polar acrylic ester polymer. This type of sorbent-material has proven to have a particularly suitable affinity towards the desired flavonoids, and an advantageous low affinity towards unwanted substances.

According to a preferred embodiment of the method according to the invention it is preferred that the sorbent-material substantially has an approximate average pore diameter of about 80–100 Å, more preferably around 85–95 Å. The desired flavonoids are estimated to have sizes around 20–40 Å. However, using a sorbent-material having too small a pore size results in a too slow absorption or even an exclusion of the flavonoids. Using too large a pore size will result in too many unwanted substances in the final product.

According to another preferred embodiment of the method according to the invention it is preferred that the sorbent-material substantially has an approximate surface area of about 200–800 $m^2/g$, preferably 400–500 $m^2/g$, and more preferably about 425–475 $m^2/g$.

According to a further preferred embodiment of the method according to the invention it is preferred that the sorbent-material substantially has an approximate pore volume of about 1.00–1.25 ml/g, preferably about 1.10–1.20 ml/g.

According to yet another preferred embodiment of the method according to the invention it is preferred that the sorbent-material substantially has an approximate and/or an average particle diameter of about 0.20–0.60 mm, preferably about 0.30–0.45 mm.

Furthermore it is preferred that the sorbent-material has a dipole momentum in the range of 1.5–2.1 and preferably about 1.7–1.9.

According to a particularly preferred embodiment of the method according to the invention, the sorbent-material meets all or most of the above mentioned specifications.

This specific combination of specifications has proven particularly suitable for extracting flavonoids from a substantially aqueous medium according to the invention.

In many cases the raw-material and/or extract further comprises an amount of polysaccharides and/or pectin which preferably may be decomposed by means of enzymes added to the raw material, extraction medium and/or the extract. However, the use of enzymes tend to decrease the yield of flavonoids.

Another preferred way of separating the pectin from the extract is to add an amount of ethanol to the extract. By adding an adequate amount of ethanol, the pectin precipitate and can be removed by e.g. centrifuging or filtering. Preferably an amount of around 35 to 75 volume-% ethanol is added to the extract, more preferably around 40 to 60 volume-% and even more preferably around 50 volume-%. The added ethanol is preferably distilled off after removal of the pectin and before the adsorption/absorption step, e.g. under reduced pressure at around 60° C.

A yet further preferred embodiment of the method is to let the polysaccharides and/or pectin stay with the extract throughout the adsorption/absorption step and to remove it from the sorbent material, e.g. by one of the above disclosed methods, after removal of the flavonoid fraction.

The separated flavonoid fraction may be extracted from the sorbent-material using various, preferably relatively polar, solvents, e.g. water mixed with acetonitrile and trichloro acetic acid, and/or mixtures of water and ethanol. However, preferably the fraction is extracted from the sorbent-material using substantially only ethanol as solvent.

Ethanol has proven to be particularly suitable for extracting the flavonoid composition from the sorbent-material, in terms of effectiveness.

Furthermore ethanol is both miscible with water in practically any ratio and is advantageously also relatively non-toxic and thus acceptable in a wide range of products in which the flavonoid composition in question is applicable. Another advantage of using ethanol is, that ethanol is easily evaporated, thus reducing cost of both sophisticated equipment and energy.

Accordingly the ethanol-phase may subsequently be evaporated to obtain a flavonoid/ethanol composition of the desired concentration or even completely evaporated to dry state. Evaporated and/or destilled-off ethanol may further be condensed and directly be re-used in the process.

An even further advantage of the method according to the invention is that the resulting flavonoid fraction is significantly more soluble in water than corresponding fractions obtained by the prior art methods.

It is believed that this latter effect is at least partly due to the fact that naturally occurring water soluble flavonoids preferably comprises a glucoside moiety. When subjecting naturally occurring flavonoids to the rather rough treatment of the prior art methods, some of the glucoside-bonds might decompose rendering the flavonoid moiety less soluble in water.

The method according to the invention seems to prevent the glucoside-bonds from decomposing, thus resulting in a flavonoid composition having significantly higher solubility in water, than flavonoids obtained by the prior art method.

It is further believed that the increased solubility in water is at least partly caused by a synergistic effect between the specific flavonoids obtainable by the method according to the invention and/or between the flavonoids and other substances present in the thus obtained composition.

The special combination of process parameters disclosed above in particular in terms of aqueous extraction within a carefully selected temperature range, and at a certain pH, a single adsorption/absorption step on the substantially aqueous extract and a retrieval of the flavonoids by preferably ethanol, seems to facilitate to production of particularly water soluble flavonoids.

Furthermore, the process according to the invention seems per se to provide a flavonoid fraction having a more suitable UV-absorption profile for use as an active ingredient in sun screen agents than flavonoids obtainable by the prior art methods and starting from the same raw material.

The flavonoid containing raw material is preferably chopped or milled before the treatment with the extraction medium.

The raw material may be used in fresh, frozen or dried state. Preferably organic raw material is frozen at some state during processing. When freezing the raw material, the cell-walls of the material tend to burst, thus facilitating the extraction of substances from within the cells.

As raw material for the process, all flavonoid comprising material may be used. Naturally it is preferred to use material containing a substantial amount of flavonoid.

Citrus fruits are known to comprise a substantial amount of flavonoids and accordingly it is preferred to use citrus fruits as raw-material for the method according to the invention. Examples of applicable citrus fruits are: Oranges, grape fruits, lemons, limes, joffa, marsh seedless chakota, khama kharta, pineapple, mandarin, kino, naragin, sautra, gallal, lime theri, pinckeo and others. Of the above mentioned marsh seedles is preferred as raw material.

It is a particular advantage of the method according to the present invention that despite that citrus fruits are known to comprise a substantial amount of skin-irritating substances, e.g. D-limonen, these substances are substantially not comprised in the composition comprising flavonoids obtainable according to the method.

Alternative material comprises e.g. leaves of citrus trees, grapes, apples, camellia flowers, yellow pepper fruit, dandelion flowers, pineapples and/or ginko biloba.

The invention also relates to a composition of flavonoids obtainable by the method according to the invention. When using citrus fruits as raw material the entire fruit or any part of the fruit may be used. Accordingly it is possible to use e.g. the juice, the peel, the flavedo or the albedo alone or in any combination.

It has been recognized that the citrus fruit Citrus Aurantium is particularly advantageous for use as raw material for the method according to the invention. *Citrus Aurantium* has surprisingly been found to contain higher levels of flavonoids than most other known citrus fruits and is thus a particularly advantageous raw material in terms of amounts of obtainable flavonoids.

It has been found that the ratio between size and level of flavonoid in *Citrus Aurantium* is most advantageous when the fruit is around 2.5–4 cm in diameter, preferably around 3–3.5 cm in diameter. When picking such relatively young and small fruits another advantage is obtained; namely that the *Citrus Aurantium* trees may be harvested more often. Furthermore less fruits are wasted due to insects, funguses and other factors, when the fruits are harvested at an early state. These advantages also applies to other young and small citrus fruits.

It is furthermore, possible to save the use of pesticides normally applied in order to let the fruits grow bigger.

Another advantage of generally using immature citrus fruits as raw material, is that the level of sugars in the fruits is lower. Accordingly the risk of decomposition reactions occurring and/or formation of caramel throughout the process is much less and the product obtained is generally whiter, i.e. more applicable in e.g. cosmetics.

Due to the gentle treatment of the raw materials by the method according to the invention, the product is generally whiter than the products obtained by the prior art methods. The typically more or less brownish compositions commercially available can be unsuited for many purposes, this being a further object solved by the method according to the invention.

Even further it has surprisingly been found that the composition of flavonoids derivable from *Citrus Aurantium* using the method according to the invention is particularly soluble in water.

It is believed that a particular synergistic effect exists between the composition of substances obtainable from *Citrus Aurantium* and in particular by the method according to the invention, thus resulting in a significantly higher solubility in water of the flavonoids comprised in the composition relative to other compositions of flavonoids.

When extracting flavonoids from citrus fruits and in particular *Citrus Aurentium* in an aqueous medium as disclosed above it has proven advantageous to apply an extraction medium temperature of around 55° C. when the fruits are smaller than around 4 cm in average diameter and a temperature of around 25° C. if the fruits are bigger than around 8 cm in average diameter. For sizes between these two sizes, it is preferable to find the optimum temperature by e.g. more or less linear interpolation within the interval 20–50° C., preferably 30–60° C.

It has furthermore, surprisingly been found that the absorption-curve of the composition of naturally occurring flavonoids found in *Citrus Aurantium* fruits substantially anticipates the degradation-curve of DNA subjected to the suns UV-light. This is particularly the case, when the flavanoids in *Citrus Aurentium* has been obtained by the process according to the invention.

Accordingly it seems that the composition of flavonoids derived from *Citrus Aurantium* in particular by the method according to the invention has per se the particularly advantageous absorbency properties.

It is thus highly advantageous to use *Citrus Aurentium* as raw material for the process according to the invention as no further steps are necessary to obtain and exploit the full advantage of the composition according to the invention as a means for absorbing UV-radiation.

Therefore it is a particularly preferred embodiment of the composition according to the invention that the composition of flavonoids is prepared from *Citrus Aurantium*. Furthermore, it is a particularly preferred embodiment of the process according to the invention that use *Citrus Aurentium* as raw material.

The invention also relates to the use of flavonoid containing extracts from *Citrus Aurentium* as a UV-absorbing ingredient in a sun screen product.

The composition according to the invention is preferably prepared by the method according to the invention. By using the method according to the invention the composition obtained is relatively water soluble and substantially free of unwanted substances.

By means of the composition comprising flavonoids according to the invention it is possible to obtain sunscreen products having superior properties than prior art sunscreen products, in terms of both efficient UV-protection of skin-cell DNA and general skin-healthcare.

Accordingly the invention also relates to the use of the composition comprising flavonoids according to the invention as a sun screen agent.

The invention further relates to a sunscreen product comprising the composition of flavonoids according to the invention and further excipients.

The term flavonoid as used herein designates all substances based on flavonol, flavone, and flavanone and their derivatives, e.g. their iso-derivatives and their glucosides. Such flavonoids comprises e.g. naringin (naringenin-7β-neohesperidoside; 5,7,4"-trihydroxyflavanone-7β-neohesperidoside), neohesperidin (hesperitin-7β-neohesperidoside; 5,7,3'-trihydroxy-4'-methoxyflavanone-7β-neohesperidoside), neoeriocitrin (eriodictyol-7β-neohesperidoside; 5,7,3',4'-tetrahydroxyflavanone-7β-neohesperidoside), isonaringin (isonaringenin-7β-neohesperidoside; 5,7,4'-trihydroxyisoflavanone-7β-neohesperidoside), rhoifolin (apigenin-7β-neohesperidoside; 4',5,7-trihydroxyflavone-7β-neohesperidoside), luteolin-7β-neohesperidoside (5,7,3',4'-tetrahydroxyflavone-7β-neohesperidoside, veronicastroside), neodiosmin (5,7,3'-trihydroxy-4'-methoxyflavone-7β-neohesperidoside), Rutin (quercetin 3β-rutinoside; 3,5,7,3',4'-pentahydroxyflavone 3β-rutinoside), Limocitrin 3-β-D-glucoside (3,5,7,4'-tetrahydroxy-8,3'-dimethoxyflavone 3β-D-glucoside), which are particularly preferred according to the invention.

The name *Citrus Aurantium* as used herein designates all citrus fruits having substantially the same composition as *Citrus Aurantium* (N.O.-Rutaceae), e.g. the species Naringa and Sevillano.

The terms aqueous and water as applied herein designates substantially pure water as well as aqueous solutions of salts, enzymes, surfactants and the like. Preferably substantially pure water is used.

BRIEF DESCRIPTION OF THE DRAWINGS

The invention will now be further illustrated by means of figures.

DETAILED DISCUSSION

FIG. 1 illustrates a preferred UV-absorption curve 1 profile for an aqueous composition comprising flavonoids according to the invention and at a total flavonoid concentration of 25 µg/ml. Preferred 20% (2 and 2') and 30%-interval (3 and 3') limits are drafted relative to the preferred UV-absorption curve profile. The preferred UV-absorption curve profile is a typical UV-absorption curve for the composition of flavonoids obtainable from *Citrus Aurantium* by the method according to the invention.

The curve's profile and corresponding 20 and 30% limits may be parallel-displaced along the UV-absorption axis depending on the concentration of the composition.

Figure 2:
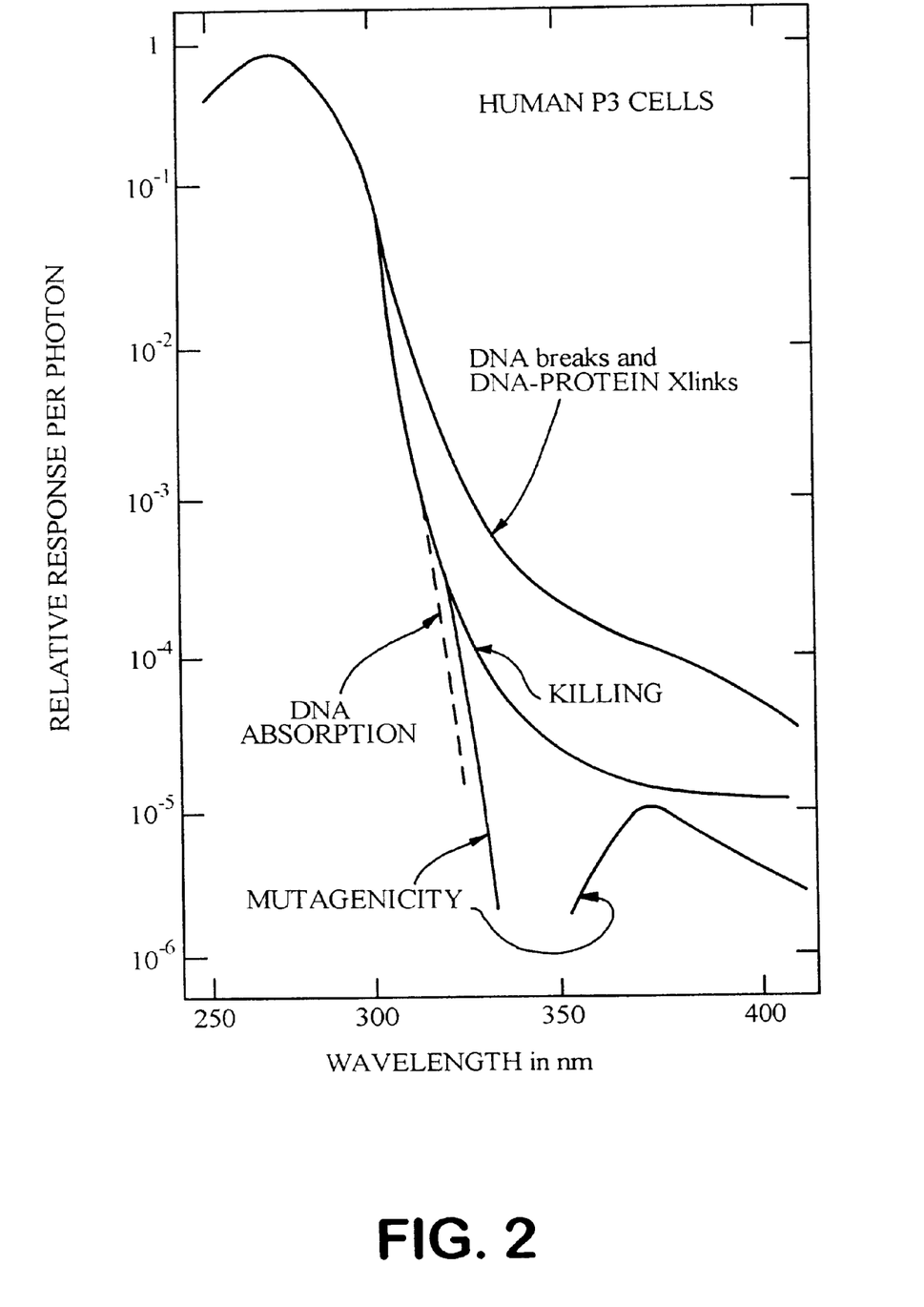
FIG. 2 shows the UV-degradation of DNA in human skin cells.

FIG. 2 illustrates the UV-degradation profile of human skin cells according to "Oxidative stress in Dermatology", Jurgen Fuchs and Lester Packer, Marcel Dekker Inc, 1993, pp. 172. According to FIG. 2 the human P3 cells (human skin cells or epithelioid cells) are most vulnerable towards UV-rays in the range 250–300 nm. In this range the DNA of the cells might break or cross link, and the cells may even die or mutate. In the range from 300–400 nm the damage induced by the UV-rays are primarily DNA-breakage and/or DNA-cross linking, which might result in long term adverse effects.

As can be seen from a comparison of the absorption curve in FIG. 1, it substantially anticipates the degradation curve in FIG. 2. Accordingly the aqueous composition of flavonoids according to the invention is extremely suitable as an active component in a sunscreen product, in terms of protecting at the wavelengths were the DNA is most vulnerable and letting the less damaging wavelengths pass, thus enabling the desired tanning of the skin.

Figure 3:
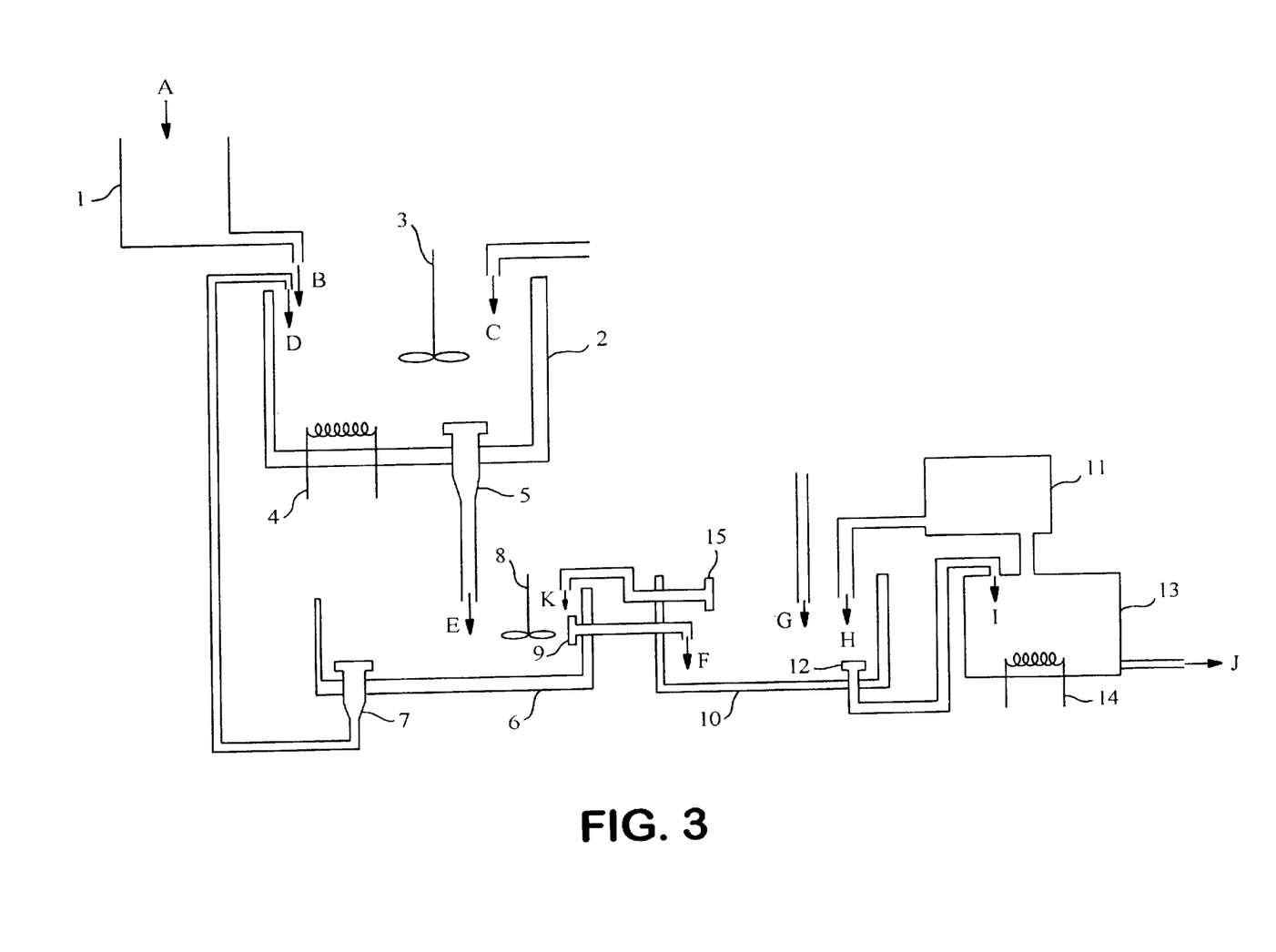
FIG. 3 is a flowchart of an apparatus for continuously carrying out the method according to the invention.

FIG. 3 illustrates a simplified flowchart of an apparatus for carrying out a preferred continuous embodiment of the method according to the invention. Optional pumps, valves and control means are not shown.

The raw material A enters a mill/homogenizer 1 where it is processed.

The processed raw material B enters the extraction reactor 2 together with fresh extraction medium C and/or optionally recycled extraction medium D. The extraction medium is stirred using a stirrer 3, and the temperature is adjusted using a temperature control device 4.

The extract in terms of flavonoid enriched extraction medium E enters continuously the separation reactor 6 through a filter unit 5 comprising a valve, in which reactor the extract is contacted with an amount of sorbent-material.

Through the filter unit 7 comprising a valve an amount of extraction medium corresponding to the amount of entering extract is continuously removed and preferably recycled to the extraction reactor or transferred to a regeneration zone (not shown). The content of the separation reactor 6 is stirred using a stirrer 8.

Through the filter unit 9 comprising a valve an amount of sorbent-material F is continuously transferred to an elution reactor 10. In the elution reactor 10 the sorbent-material is contacted with an amount of fresh solvent G and/or and amount of recycled solvent H entering from a condenser 11.

Through the filter unit 12 comprising a valve an amount of solvent corresponding to the amount of flavonoid enriched solvent I entering the reactor 10 is continuously transferred to an evaporator 13, where the solvent is heated by means of a temperature control device 14 and where the solvent is partly evaporated, in order to concentrate the product J.

Through the filter unit 15 comprising a valve an amount of sorbent-material K corresponding to the amount of sorbent-material entering the reactor 10 is continuously recycled to the separation reactor 6. The concentrated product J is removed and the evaporated solvent is transferred to the condenser 11 and recycled to the elution reactor 10.

Figure 4:
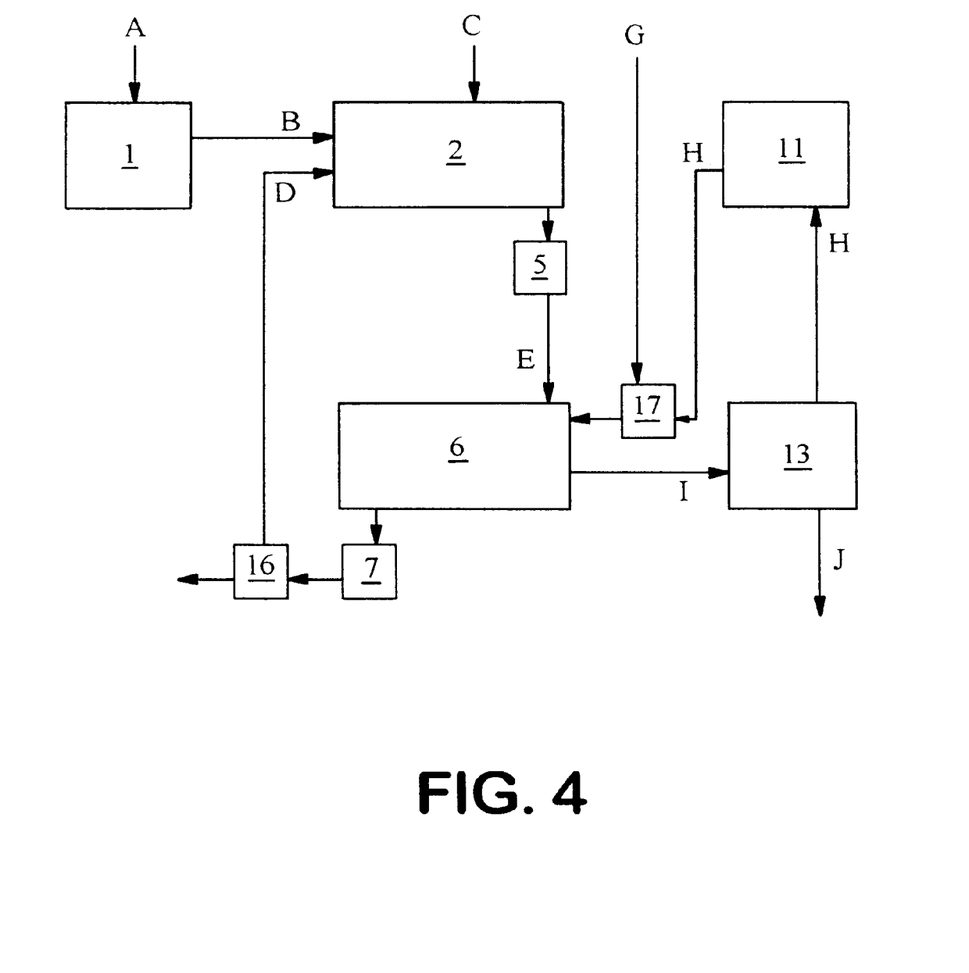
FIG. 4 is a flowchart of an apparatus for carrying out the method according to the invention batch wise.

FIG. 4 illustrates a simplified block diagram of an apparatus for carrying out a preferred embodiment of the method according to the invention batch-wise. Optional pumps, valves and control means are not shown.

The raw material A enters a mill/homogenizer 1 where it is processed.

The processed raw material B enters the extraction reactor 2 together with fresh extraction medium C and/or optionally recycled extraction medium D. The extraction medium is stirred using a stirrer (not shown), and the temperature is adjusted using a temperature control device (not shown).

When the equilibrium of flavonoids in the extract is reached the extract E is transferred to a sorbent containing separation reactor 6 through a filter unit 5. The content of the separation reactor 6 is stirred using a stirrer (not shown).

When the equilibrium of flavonoids in the extract in the separation reactor 6 is reached the used extraction medium is removed through the filter unit 7 and the valve 16 and optionally recycled to the extraction reactor or transferred to a regeneration zone (not shown) through the valve 16.

Through the valve 17 an amount of solvent G/H enters the reactor 6, and the content of the reactor is stirred using a stirrer (not shown). When the equilibrium of flavonoids in the solvent in the separation reactor 6 is reached the flavonoid enriched solvent I is transferred to an evaporator 13, where the solvent is heated by means of a temperature control device (not shown) and where the solvent is partly evaporated, in order to concentrate the product J.

The concentrated product J is removed and the evaporated solvent H is transferred to the condenser 11 and recycled to the separation reactor 6, through the valve 17.

The invention will now be further illustrated by means of examples:

EXAMPLE 1

Example 1 is an example of an embodiment according to the invention performed using an apparatus similar to the apparatus disclosed in the flowchart in FIG. 3.

About 2500 kg of hole frozen *Citrus Aurantium* is milled in a mill. The thus processed *Citrus Aurantium* is transferred to a 15000 l extraction reactor, where it is mixed with about 10000 l of water and heated to about 50° C. and thermostated at this temperature. The extraction reactor content is stirred.

The thus obtained extract in terms of flavonoid enriched extraction medium is led to a 5000 l separation reactor at a rate of about 50 l/min through a filter unit, in which reactor the extract is brought in contact with about 500 kg Amberlite™ XAD-7 sorbent -material (CAS-number 37380-43-1).

The separation reactor content is stirred, and an amount of about 50 l/min of the extraction medium is led out of the separation reactor and recycled to the extraction reactor.

Continuously an amount of about 5 kg/min of the sorbent-material is led from the separation reactor to a elution reactor in which the sorbent-material is mixed with an amount of ethanol which is supplied to the elution reactor in an amount of about 20 l/min. An amount of sorbent-material corresponding the incoming amount of sorbent-material is returned from the elution reactor to the separation reactor, and an amount of flavonoid enriched ethanol corresponding to the incoming amount of ethanol is led from the elution reactor to an evaporator.

In the evaporator about 20 l/min of ethanol is evaporated, and the thus obtained concentrated product is removed.

The about 2500 kg *Citrus Aurantium* results in about 35–40 kg pulverous composition comprising flavonoids or a corresponding amount of solubilized composition in ethanol at any desired concentration.

The evaporated ethanol is condensed in a condenser and recycled for use in the elution reactor.

The continuous process as disclosed in the present example has the advantage, that relatively small reactors may be used, thus reducing cost of the apparatus.

EXAMPLE 2

Example 2 is an example of an embodiment according to the invention performed using an apparatus similar to the apparatus disclosed in the flowchart in FIG. 4.

About 2500 kg of frozen *Citrus Aurantium* is milled in a mill. The thus milled *Citrus Aurantium* is transferred to a 30000 l extraction reactor, where it is mixed with about 25000 l of water and heated to about 50° C. and thermostated at this temperature.

The extraction reactor content is stirred, and extract samples are continuously tested for UV-absorption. At UV-absorption equilibrium (when the UV-absorption at 282 nm no longer rises significantly), the extract in terms of flavonoid enriched extraction medium is led to a 30000 l separation reactor through a filter unit, in which reactor the extract is brought in contact with about 1000 kg Amberlite™ XAD-7 sorbent-material (CAS-number 3738043-1).

The separation reactor content is stirred, and extract samples are continuously tested for UV-absorption. At UV-absorption equilibrium (when the UV-absorption at 282 nm no longer lowers significantly), the extraction medium is led out of the separation reactor.

The extraction medium is subsequently optionally reused in the extraction process.

An amount of 25000 l ethanol is led to the separation reactor as a solvent for the flavonoid comprising composition. The content of the reactor is stirred, and solvent samples are continuously tested for UV-absorption. At UV-absorption equilibrium (when the UV-absorption at 282 nm no longer rises significantly), the flavonoid enriched solvent is led to an evaporator in which the solvent is evaporated and the product is concentrated to obtain about 35–40 kg pulverous composition comprising flavonoids or a corresponding amount of solubilized composition in ethanol at any desired concentration.

The evaporated solvent is condensed in a condenser and optionally reused in the process.

EXAMPLE 3

A solubility experiment was carried out in which commercially available naringin was dissolved in water at room temperature. The naringin was dissolved in an amount of 0.1 g/l corresponding to around 0.01 weight-%.

A pulverous test sample of a composition obtained from *Citrus Aurantium* by the method according to the invention and comprising about 20 weight-% naringin was also dissolved in water at room temperature. The composition was dissolved in an amount of 180 g/l, corresponding to a 3% solution of naringin weight-%.

Accordingly the solubility of naringin is 300 times higher in water when obtained by the method according to the invention and being in the composition obtained from *Citrus Aurantium* by said method, than commercially available naringin.

What is claimed is:

1. A composition comprising flavonoids including at least one flavanone selected from the group consisting of naringin, neohesperidin, neoeriocitrin and isonaringin, and at least one flavone comprising rhoifolin, said composition having a UV-absorbency at 282 nm in water where said at least one flavanone accounts for 75–98% of UV-absorbency of said flavonoids, and where flavones accounts for 2–25% of UV-absorbency of said flavonoids at 282 nm.

2. A composition according to claim 1, wherein the at least one flavanone has an absorption profile substantially as naringin and neohesperidin and the flavones have an absorption profile substantially as rhoifolin.

3. A composition according to claim 1, wherein said at least one flavanone is selected from the group consisting of naringin and neohesperidin.

4. A composition according to claim 1, including the flavonoids naringin, neohesperidin, neoeriocitrin, isonaringin and rhoifolin.

5. A composition according to claim 1, wherein the flavanoids naringin and neohesperidin account for 60–80% of the UV-absorption, neoeriocitrin accounts for 5–15% of the UV-absorption, isonaringin accounts for 1–10% of the UV-absorption and rhoifolin accounts for 1–10% of the flavonoids UV-absorption at 282 nm in aqueous solution.

6. A composition comprising one or more flavonoids, including at least one flavanone selected from the group consisting of naringin, neohesperidin, neoeriocirin and isonaringin, and at least one flavone comprising rhoifolin, said composition having a UV-absorption profile in water in the wavelength range 270–360 nm and at a total flavonoid concentration of 25 µg/ml, said profile substantially falling within the +/−30% limits of the profile in FIG. 1.

7. A composition comprising one or more flavonoids, including at least one flavanone selected from the group consisting of naringin, neohesperidin, neoeriocirin and isonaringin, and at least one flavone comprising rhoifolin, said composition exhibiting an absorption ratio of 1.8–2.4 between the UV-absorption 282 nm and the average UV-absorption at 320–324 nm in water.

8. A method of preparing a composition according to claims 1, 6 or 7 comprising flavonoids, wherein a flavonoid-containing raw material in the form of immature citrus fruit is treated with an extraction medium to obtain an extract from which said composition is separated by absorption and/or adsorption, comprising the steps of a) contacting the immature citrus fruit with an aqueous extraction medium at a temperature between 20 and 60° C. and at a pH at or below 7 to extract flavonoids into the extraction medium, b) separating the flavonoids from the extraction medium by adsorption or absorption by means of a sorbent-material at a pH below 7, and c) obtaining the flavonoids from the sorbent-material by means of a solvent.

9. A method according to claim 8, wherein the extraction medium is substantially pure water.

10. A method according to claim 8, wherein the temperature of step a) is between 20 and 30° C. if the average diameter of the citrus fruit is above 8 cm, between 50 and 60° C. if the average diameter of the citrus fruit is below 4 cm and between 30 and 50° C. if the average diameter of the citrus fruit is between 4 and 8 cm.

11. A method according to claim 8, wherein the pH value of the extraction medium in step a) is between 1 and 6.

12. A method according to claim 11, wherein the pH value of the extraction medium in step a) is between 2 and 5.

13. A method according to claim 8, wherein the sorbent-material is a non-ionic polymeric adsorbent.

14. A method according to claim 8, wherein the average size of the pore diameters of the sorbent-material is between 8–100 Å.

15. A method according to claim 8, wherein the sorbent-material has a surface area of about 400–500 m2/g.

16. A method according to claim 8, wherein the sorbent-material has a pore volume of about 1.00–1.25 ml/g.

17. A method according to claim 8, wherein the sorbent-material has an average particle diameter of about 0.20–0.60 mm.

18. A method according to claim 8, wherein the dipole momentum of the sorbent-material is in the range of 1.5–2.1.

19. A method according to claim 8, wherein the extract is filtered before bringing it in contact with the sorbent-material.

20. A method according to claim 8, wherein the composition comprising flavonoids is extracted from the sorbent-material using a polar solvent.

21. A method according to claim 8, wherein the composition comprising flavonoids is extracted from the sorbent-material using a solvent consisting essentially of ethanol.

22. A method according to claim 8, wherein the raw-material and/or extract is treated with an amount of enzyme.

23. A method according to claim 8, comprising the steps of mixing the extract with ethanol to precipitate pectin, and substantially removing the precipitated pectin prior to the adsorption/absorption.

24. A method according to claim 8, wherein the raw-material is milled and/or chopped in fresh, frozen or dried state.

25. A method according claim 8, wherein the raw-material comprises *Citrus Aurantium*.

26. A sunscreen product comprising a composition of flavonoids according to claims 1, 6 or 7.

27. A sunscreen product according to claim 26 in the form of a gel and/or is substantially water based.

* * * * *